Figure 1:
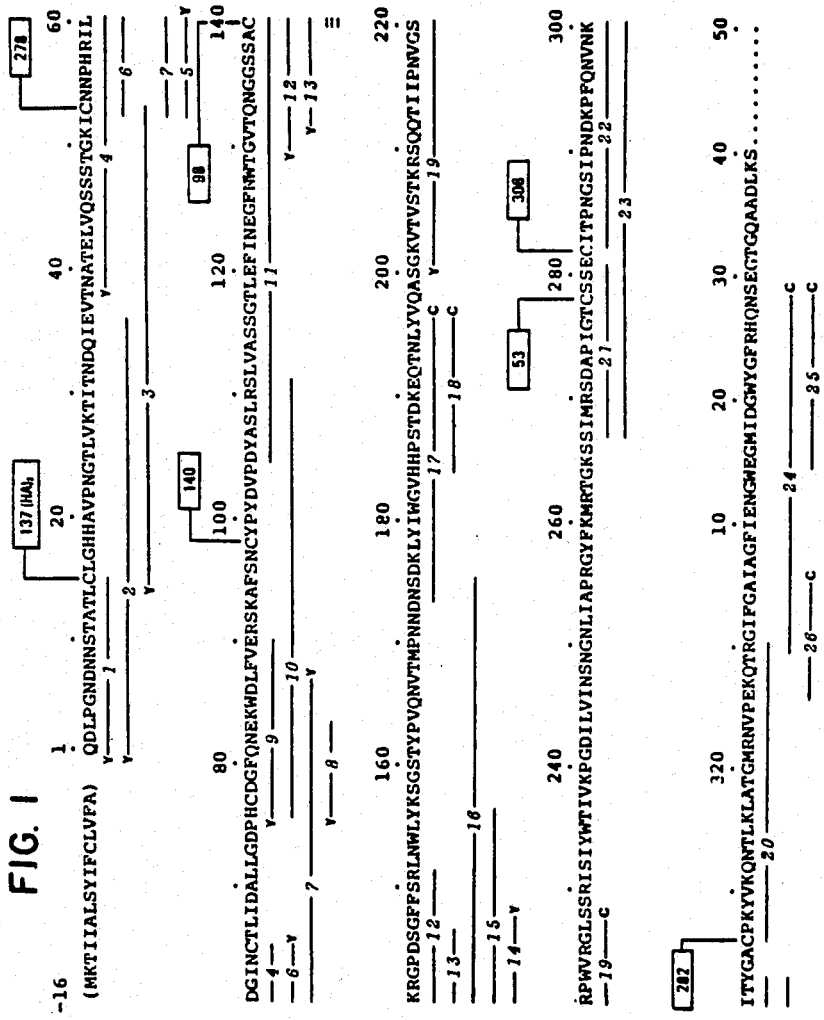

United States Patent [19]

Green et al.

[11] Patent Number: 4,625,015

[45] Date of Patent: Nov. 25, 1986

[54] BROAD SPECTRUM INFLUENZA ANTISERA

[75] Inventors: Nicola Green, La Jolla; Stephen Alexander, San Diego, both of Calif.

[73] Assignee: Scripps Clinic & Research Foundation, La Jolla, Calif.

[21] Appl. No.: 527,401

[22] Filed: Aug. 29, 1983

Related U.S. Application Data

[63] Continuation-in-part of Ser. No. 410,455, Aug. 23, 1982, abandoned.

[51] Int. Cl.[4] .......................... C07K 7/06; C07K 7/10; C07K 17/02; A61K 39/145
[52] U.S. Cl. .................................... 530/324; 530/328; 530/387; 530/403; 424/88; 424/89; 424/86; 424/85
[58] Field of Search .................... 260/112.5 R, 112 R; 424/89, 88, 85, 86

[56] References Cited

PUBLICATIONS

Müller, G. et al., Proc. Natl. Acad. Sci., vol. 79, pp. 569–573, 1982.
Green, N. et al., Cell, vol. 28, pp. 477–487, 1982.
Jackson, D. et al., Virology, vol. 120, pp. 273–276, 1982.
Min Jou, W. et al., Cell, vol. 19, pp. 683–696, 1980.
Arcus et al., Intervirology, 15, 145 (1981).
Lamb et al., Nature, 300, 66 (1982).
Wabuke-Bunoti et al., J. Immunol., 130, 2386 (1983).

*Primary Examiner*—Blondel Hazel
*Attorney, Agent, or Firm*—Dressler, Goldsmith, Shore, Sutker & Milnamow Ltd.

[57] ABSTRACT

Antisera against synthetic peptides which neutralize influenza viruses of differing hemagglutinin subtypes, provide protection against infection by influenza virus and methods of preparing the same are disclosed.

9 Claims, 3 Drawing Figures

BROAD SPECTRUM INFLUENZA ANTISERA

CROSS-REFERENCE TO RELATED APPLICATION

This is a continuation-in-part of copending application Ser. No. 410,455 filed on Aug. 23, 1982 now abandoned.

TECHNICAL FIELD

This invention relates to immunochemistry, and, more specifically, to immunological reagents and reactions involving influenza viruses.

BACKGROUND ART

Influenza remains a major epidemic disease worldwide despite intensive vaccination programs. Webster et al., Nature, 296, 115-121 (1982) and Palese et al., Science, 215, 1469-1474 (1982). To date, vaccines for these efforts have utilized whole virus as antigen to elicit antibody responses against the particular influenza strain in circulation. Tyrrel et al., Br. Med. Bull., 35, 77-83 (1979).

These conventional vaccines suffer from several standpoints including poor characterization and non-uniformity due to production of virus in embryonated eggs, and can cause serious adverse side reactions. Most importantly, they suffer from a lack of generality required to be effective against the broad spectrum of influenza strains which can arise by genetic recombination. A well-defined vaccine which eliminates these problems is needed.

More recent work by Müller et al., Proc. Natl. Acad. Sci. USA, 79, 569-573 (January 1982), utilizing peptides as immunogens has been reported. In that work, immunogens were prepared utilizing a synthetic peptide corresponding to positions 91-108 of the $HA_1$ subunit (the amino-terminal subunit) of the hemagglutinin (HA) molecule of a type A (H3N2) influenza virus. Müller et al. were able to provide a low level of neutralizing activity with sera obtained by immunizing with their peptide. In addition, Jackson et al., Virology, 120, 273-276 (1982) used a synthetic peptide whose amino acid residue sequence corresponded to positions 123-151 of the $HA_1$ of the X-31 (H3N2) strain to raise antibodies that recognized the immunogenic peptide, but did not appear to bind to the virus itself.

We here present neutralization and protection studies utilizing antisera prepared against synthetic peptides corresponding to a number of regions of the influenza hemagglutinin (HA) molecule and describe and claim peptides, antisera and methods which are more efficient and well-characterized alternatives to standard, whole virus influenza vaccines and immunochemical methods.

The primary target of the neutralizaing response of vaccination is the hemagglutinin molecule which is the major surface glycoprotein of the virus. Dowdle et al., J. Virol., 13, 269-275 (1974). This hemagglutinin is synthesized in vivo as a precursor molecule (HA), and is subsequently cleaved proteolytically to two subunits, $HA_1$ and $HA_2$. Cleavage is necessary for the virus to be infective. Klenk et al., J. Virol., 69, 426-439 (1975) and Lazarowitz etal., Virology, 68, 440-454 (1975).

The sequences of the HA genes of several epidemic strains of influenza have been described and indicate that there is rapid genetic variation occurring within these genes. Laver et al., Nature, 283, 454-457 (1980); Webster et al, Virology, 104, 139-148 (1980); Wiley et al., Nature, 289, 373-378 (1981); and Gething et al., Nature, 187, 373-378 (1981). These mutational changes are reflected as alterations of the antigenic structure of HA allowing escape of the virus from the protection of the previous immunization, and the subsequent rise of a new epidemic strain. Moreover, serologically distinct viruses from previous epidemics occasionally reenter the population, possibly from non-human hosts, where they may have undergone genetic recombination.

It has been previously demonstrated that synthetic peptides corresponding to virutally all regions of the X-47 influenza virus HA (H3N2) [Min-Jou, Cell, 19, 683-696 (1980)] are capable of eliciting an immune response in experimental animals. Green et al., Cell, 28, 477-487 (1982). The antisera react strongly with the respective peptides, and in most cases also react with the homologous purified hemagglutinin molecule and the intact virus. Green et al., Cell, 28, 477-487 (1982) and Müller et al., Proc.Natl. Acad.Sci. USA, 79, 569-573 (1982).

The present results indicate that some antisera to synthetic peptides representing both the $HA_1$ and $HA_2$ subunits are capable of neutralizing X-47 influenza virus replication, and more importantly, are capable of protecting animal hosts from the disease caused by that virus. Moreover, these results also demonstrate that some sera against the synthetic peptide analogs of the influenza virus HA are capable of neutralizaing virus infections of differing hemagglutinin subtype.

STATEMENT OF THE INVENTION

Antibodies made against synthetic peptides representing virtually all regions of the X-47 (H3N2) influenza virus hemagglutinin were [Min-Jou, Cell, 19, 683-696 (1980)] tested for their ability to neutralize virus infection in vitro. Some of the peptide immunogens elicited antibody responses which effectively neutralize both the homologous viruses and, more importantly, several strains of the $H_1$ subtype which have been shown to be the most divergent influenza A subtype from our prototype $H_3$ virus. Webster et al., Nature, 296, 115-121 (1982). Neutralization by combinations of antisera was not synergystic, but rather the simple sum of the titers of the component sera. Moreover, use of the petpdies of this invention in vaccines leads to the protection of animals infected with influenza virus.

Those synthetic immunogens which gave a neutralizing response fell into two general classes: (1) those which contained a cysteine residue which is part of a disulfide bridge in the native molecule; and (2) those which bordered or spanned the site of cleavage of the precursor hemagglutinin to the mature (and functional) subunit form.

Although the only logic behind the choice of peptide immunogens was that some of the sequence be exposed on the surface of the molecule, the results outlined above indicate that other criteria should be considered when designing synthetic antigens with possible use as vaccines, viz: (1) special attention should be paid to regions of the target molecule which are functionally active; and (2) peptides may be considerably shorter than those in this study, and should be more symmetrical around cysteine residues. Moreover, multivalent synthetic antigens should produce more effective neutralizing titers. The results indicate that these antigens may be used to produce safe and generalized vaccines against influenza.

We have also discovered that certain peptides, particularly synthetic peptides (built-up from component amino acid residues) as compared to those materials cleaved from the hemagglutinin molecule or those prepared by recombinant DNA technology, are capable of eliciting the production of antibodies that neutralize more than one strain of influenza virus, and consider that neutralization a useful step in the prevention and treatment of influenza. Each of the peptides of this invention has a molecular weight less than that of the intact hemagglutinin molecule, and typically has a length of about 8 to about 40 amino acid residues. The specific synthetic peptides which have been found to be most effective have amino acid residue sequences that correspond to portions of the influenza hemagglutinin molecule amino acid residue sequence. Those peptides are defined by the following amino residue acid sequence formulas, from left to right and in the direction of amino-terminus to carboxy-terminus:

(a) SIMRSDAPIGTCSSECITPN-GSIPNDKPFQNVNKITY;

(b) RGIFGAIAGFIENGWEGMIDG-WYGFRHQNC; and (c) EKQTRGIFGAC.

As noted hereinafter, some of the synthetic peptides such as (b) and (c) above were prepared to contain an added cysteine (C) or tyrosine (Y) residue at either of the amino- or carboxy-terminii. The presence of those added amino acid residues is not necessary to the invention, and as a consequence, they may be omitted from the amino acid residue sequences of this invention.

One additional synthetic peptide whose amino acid residue sequence corresponds to positions 306–330, the carboxy-terminus, of the $HA_1$ molecule has also been found to (a) stimulate T-cell proliferation, (b) induce production of antibodies that cross-react with influenza strains other than X-47, as well as (c) protect animals from challenge with live virus when used in a vaccine. The amino acid residue sequence of that peptide, from left to right and in the direction from amino-terminus to carboxy-terminus, is shown in the formula below:

(d) CPKYVKQNTLKLATGMRNVPEKQTR.

Another peptide also induces the production of neutralizing antibodies to strain X-47 as well as antibodies that cross-react and neutralize, to some extent, other influenza strains. The amino acid residue sequence of this peptide, from left to right and in the direction of amino-terminus to carboxy-terminus, is shown in formula (e) below:

(e) CNNPHRIL.

Two cyclic or oligomeric peptides have also been prepared that have neutralizing properties. These peptides are in cyclized or oligopolymerized form, made through oxidized mercapto moieties of both the amino- and carboxy-terminal cysteine residues. The amino acid residue sequences of these peptides, from left to right and in the direction of amino-terminus to carboxy-terminus, are shown in their unoxidized forms by the formulas below:

(f) CPKYVKQNTLKLATGMRNVPEKQTRC; and (g) CKRGPDSGFFSRLNWLYKSGSC.

This invention comprises, as compositions of matter, amino acid residue sequences containing the above defined peptides, or portions thereof, produced synthetically or isolated from proteins, and may be used either alone or together. Synthetic peptides are preferred. This invention also comprises the antisera resulting from the challenge of an organism by one or more peptides containing the above defined peptides, and compositions in which antibodies to the above peptides, alone or combined, are an immunologically active agent. This invention further contemplates the processes of preparation of these compositions and the use of these compositions in immunological diagnosis or treatment. For example, this invention in one facet comprises vaccines for use in conventional innoculation or ingestion or inhalation vaccination in which an immunologically active agent induced in the immunized host is one or more antibodies to the above defined peptides.

BRIEF DESCRIPTION OF THE DRAWINGS

In the drawings forming a part of this disclosure:

FIG. 1 depicts the amino acid residue sequence of the X-47 HA molecule derived from the neucleotide sequence [Min-Jou et al., *Cell,* 19, 683–696 (1980)];

FIG. 2 depicts the results of the micro-titration of X-47 influenza virus on Madin-Darby canine kidney (MDCK) epithelial cells; and FIG. 3 depicts the neutralization of X-47 virus by combinations of anti-peptide antisera.

DESCRIPTION OF THE BEST MODE

The full names for individual amino acid residues are sometimes used herein as are the well-known three-letter abbreviations. The one-letter symbols for amino acid residues are used most often. The Table of Correspondence, below, provides the full name as well as the abbreviation and symbols for each amino acid residue named herein.

Table of Correspondence

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Referring to FIG. 1, the amino acid residue sequence of the X-47 HA molecule [Min Jou et al., *Cell,* 19, 683–696 (1980)] is depicted. The entire $HA_1$ and the amino-terminus of $HA_2$ are shown. The lines under the sequence represent the peptides which were synthesized and used for immunization. C or Y at ends of those lines represent additions of cysteine or tyrosine not found in the primary sequence. Disulfide bonds are indicated C -□. Antisera were prepared in rabbits against the coupled to keyhole limpet hemocyanin (KLH) as described in Green et al., *Cell,* 28, 477–487 (1982), except where indicated as free, see FIG. 3 and Table 1. Synthetic peptides and vaccines including them were also prepared as described by Green et al., above, whose disclosures are incorporated herein by reference.

A. Neutralization assay

To pursue the testing of large numbers of anti-peptide antisera, we developed a rapid quantitative in vitro assay for influenza virus which can be performed in less time than required for conventional plaque assays. Kilbourne, in *Fundamental Techniques in Virology*, (eds. Habel, K. and Salzwan, N. P.) pages 146-160, (Academic Press, New York, 1969). Forty virus titations or as many as 80 serum neutralizations can be performed in one-half of one day. Moreover, a number of experimental variables which might occur from day to day are eliminated, since many viruses or sera can be titrated in a single day. The assay is reproducible and the end point is proportional to the original inoculum of virus.

Figure 2:
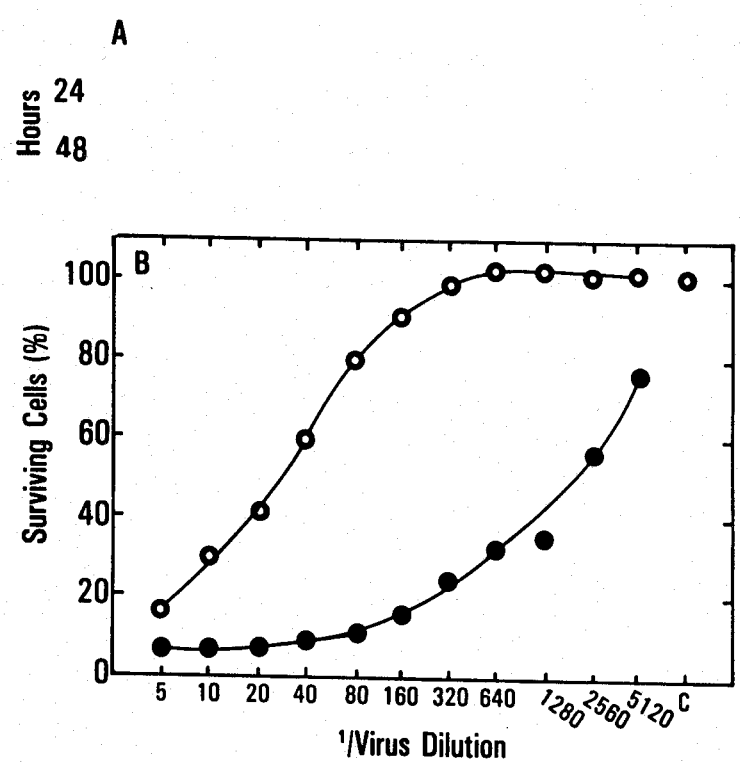

The data shown in FIG. 2 were generated as follows: Micro-titration of X-47 influenza virus on Madin-Darby canine kidney (MDCK) epithelial cells. MDCK cells were grown in Minimal Eagles medium (MEM) supplemented with 10% fetal calf serum; penicillin (100 units/-milliliter), streptomycin (100 grams/milliliter), 4 millimolar L-glutamine, 1 millimolar Na-pyruvate, 0.075% tryptose phosphate broth (Difco) and 0.5% glucose. Following trypsinization and washing in medium, the cells were suspended to a final concentration of $10^6$ cells/milliliter in growth medium. 50 Microliters of the suspension were added to each well of a 96 well flat-bottomed microtiter plate (Falcon) containing an additional 50 microliters medium. The plates were incubated overnight at 37° C. allowing cell attachment for either virus or serum titrations on the following day.

Virus was titrated by making 50 microliter two-fold serial dilutions in a 96 well microtiter plate in MEM containing antibiotics (dilution medium). An additional 50 microliters of dilution medium were added to each well and the plate was incubated for 60 minutes at 37° C. (mock neutralization). The medium covering the MDCK cell monolayers in the 96 well plate was aspirated and the cells were washed with 100 microliters of dilution medium.

The titrated virus was then transferred to the corresponding wells of the plate containing the washed MDCK cells. The virus was allowed to absorb for 60 minutes at 37° C., whereupon it was removed, and the cells were washed with 100 microliters of diultion medium. The cells were then overlayed with 100 microliters of overlay meidum consisting of Basal Medium (Eagle) containing antibiotics, 0.005% DEAE-dextran (Pharmacia), 2 millimolar L-glutamine, 0.05% fetal calf serum and 2 micrograms per milliliter trypsin (type III, 2×crystalized, Sigma).

The cells were incubated for 48 hours, at which time they were observed microscopically for cytopathic effect (CPE), and were subsequently stained with 0.1% crystal violet in 20% ethanol, followed by rinsing in tap water. Each virus was screened for the last dilution which gave complete lysis of the MDCK monolayer in 48 hours and this dilution was used in subsequent tests for antibody neutralization.

FIG. 2A shows one and two day (24 and 48 hour) end points for a titration of X-47 virus. The end points of the CPE are quite easy to score visually. The plates can be mechanically read in a microtiter plate reader and the results plotted graphically as shown in FIG. 2B. A two-day assay was chosen because it was found that the virus inoculum needed from a complete CPE in 48 hours allowed the best overall sensitivity in testing the neutralizing strenghts of the anti-peptide antisera.

FIG. 2B shows graphical displays of the stained plates in FIG. 2A after reading in a Titertek Multiskan apparatus with a 492 nanometer filter. The extent of CPE was expressed as percent of the control well (C) which received no virus. Open and closed circles are the 24 and 48 hour end points, respectively. The CPE end point dilutions for X-47 virus are 1:5 and 1:300 for 24 and 48 hours respectively.

The assay is based on the cytopathic effect (CPE) of influenza virus on monolayers of Madin-Darby canine kidney epithelial (MDCK) cells. Gaush et al., *Applied Microbiology,* 16, 588–594 (1968).

The neutralization assay is accomplished by making serial dilutions of the sera in microtiter plates and then adding to each well an aliquot of virus at the dilution previously shown by titration to give a complete CPE in 48 hours. Thus for X-47 virus this was a 1:300 dilution of allantoic fluid. We have determined that this is approximately 10,000 plaque-forming units per well.

Data depicted in FIG. 3 were obtained using the same general techniques described as to FIG. 2. Sera were titrated by making 50 microliter two-fold dilutions in a 96 well plate followed by addition of 50 microliters of the appropriately diluted (1:300 from FIG. 2) virus. After 60 minutes of incubation at 37° C., each serum-virus mixture was transferred to the corresponding well of the 96 well plate containing monolayers of washed MDCK cells. The remainder of the technique is as in FIG. 2. The control well (C) contained no serum or virus.

FIG. 3 depicts results of neutralization of X-47 virus by combinations of anti-peptide antisera. NRS (Normal rabbit serum) indicates that the anti-serum being tested was diluted with an equal volume of normal rabbit serum to compensate for the dilution factor when antisera were tested in combination. Titers are expressed as the point of 50% neutralization as described in Table 1. The antisera are, (●) anti-X47 virus; (□) normal rabbit serum; (O) anti-peptide 23; (Δ) anti-peptide-24; and (◆) anti-peptide−23 and −24.

The results, set forth in Table 1, show that a number of peptides elicit antibodies with in vitro neutralizing activity against X-47 virus (H3N2).

TABLE 1

Neutralization of X-47 Virus by Anti-Peptide Antisera[a]

| Antiserum[b] | Neutralization titer[c] |
|---|---|
| 1 | 0[d] |
| 2 | 5–10 |
| 3 | 0 |
| 4 | 0 |
| 5 | 20–40 |
| 6 | 5–10 |
| 7 | 5–10 |
| 8 | 0 |
| 9 | 0 |
| 10 | 0 |
| 11 | 0 |
| 12 | 0 |
| 13 | 0 |
| 14 | 0 |
| 15 | 0 |
| 16-free | 5–10 |
| 17-free | 0 |
| 18 | 5 |
| 19 | 0 |
| 20 | 10–20 |
| 21 | 10–20 |

TABLE 1-continued

| Neutralization of X-47 Virus by Anti-Peptide Antisera[a] | |
|---|---|
| Antiserum[b] | Neutralization titer[c] |
| 22 | 20–40 |
| 23-free | 20–40 |
| 24-free | 20–40 |
| 25 | 5 |
| 26 | 40–80 |
| X-47 | 1260 |

Figure 3:
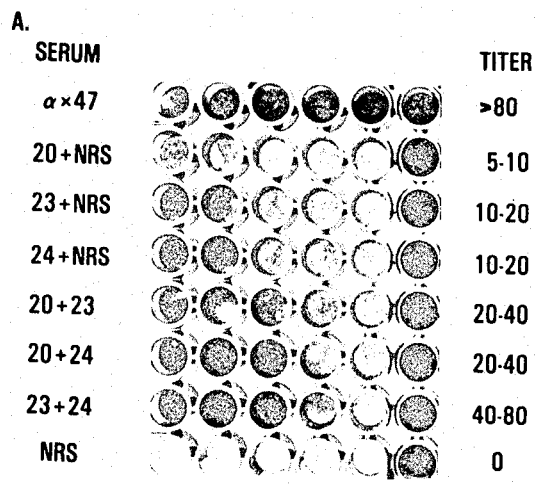
Figure 3:
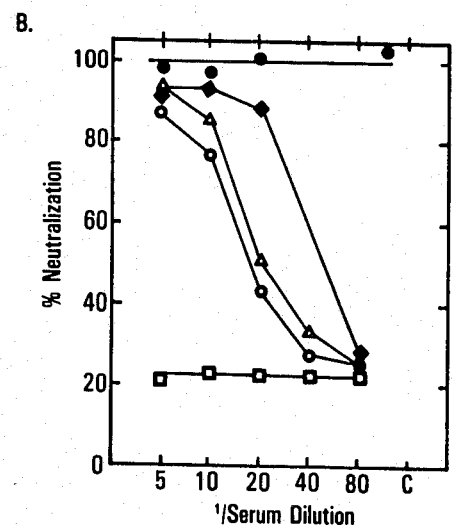

[a]Details of the neutralization assay are presented above in reference to FIG. 3.
[b]These numbers refer to the antiserum against the peptide with the corresponding number as shown in FIG. 1.
[c]The titer is taken as the reciprocal of the range of serum dilutions where the CPE was inhibited to 50% of the control. The data are representative of four experiments.
[d]A titer of zero was assigned when even the highest concentration of antiserum; i.e., undiluted, showed no sign of protection relative to normal rabbit serum controls.

The above-studied peptides seem to cluster into two distinct groups with respect to their positions in the hemagglutinin molecule. Those groups are:

1. Regions of the molecule containing disulfide bridges including:
   a. The proposed antigenic site "C" of Wiley et al. [Wiley et al., Nature, 289, 373–378 (1981)], which is a protruding bulge in the molecule formed by a disulfide bond between cysteine 53 and cysteine 278. Peptides in the regions of cysteine 53 (peptides 5, 6, and 7) and cysteine 278 (peptides 21 and 23) elicited neutralizing antibodies.
   b. The disulfide bridge between cysteine 282 and cysteine 306. Antisera against peptides 22 and 20 which encompass these cysteines were neutralizing.
   c. The disulfide bridge between cysteine 15 of $HA_1$ cysteine 137 in $HA_2$. Although we have not synthesized a peptide containing the latter cysteine, antisera against peptide 2 do give a low neutralizing titer.
2. The region surrounding the site of cleavage of the precursor HA into $HA_1$ and $HA_2$. Garten et al., Virology, 115, 364–374 (1981). Thus, antiserum against the carboxy-terminus of $HA_1$ (peptide 20) and the amino-terminus of $HA_2$ (peptide 24, and to a lesser extent peptide 25) were neutralizing. In addition, a peptide representing the cleavage site in the precursor HA (peptide 26) also provided a neutralizing response.

Indeed, the hydrophobic amino-terminus of $HA_2$ is the most highly conserved sequence in HA. Waterfield et al., Br.Med.Bull., 35, 47–63 (1979). It is similar to the amino-terminus of the $F_1$ component of the Sendai virus fusion glycoprotein [Gething et al., Proc.Natl.Acad.Sci. USA, 75, 2737–2740 (1978)] and thus may be involved in early steps of influenza replication involving membrane fusion. Although the $HA_2$ amino-terminus is buried in the HA trimer, [Wilson et al., Nature, 289, 66–73 (1981)] it has recently been shown there is a conformational change in the molecule at the pH which allows fusion [Skehel et al., Proc.Natl.Acad.Sci., 79, 968–972 (1982)] which is thought to expose parts of the molecule, including the amino-terminus of $HA_2$ [Richardson et al., Virology, 105, 205–222 (1980)].

In all cases, the neutralizing titers of the antipeptide sera are less than that of the serum made against intact X-47 viruses. Therefore, it was of interest to see what effect combinations of antipeptide sera would yield. FIG. 3 presents neutralization of X-47 by combinations of antipeptide antisera which have individually demonstrated the highest neutralizing activity.

The data indicate that there is no synergistic effect of combining sera. The titers are the simple sum of their parts, indicating that they are acting independently. Titers of sera against nested peptides from a common sequence are not additive. Antisera with no neutralizing activity when tested in combination do not show neutralizing activity, nor are they stimulated by sera with neutralizing capacity.

B. Cross-Reactivity With Other Influenza Viruses

The amino acid sequences of a number of influenza virus HA molecules have been derived from the nucleotide sequences of their HA genes. Considerable conservation exists among the sequences despite variation in HA subtype. Webster et al., Nature, 296, 115–121 (1982); Laver et al., Nature, 283, 454–457 (1980); Webster et al, Virology, 104, 139–148 (1980); Wiley et al., Nature, 289, 373–378 (1981); and Gething et al., Nature, 187, 373–378 (1981). These regions include those for which we have demonstrated neutralizing activity with our antipeptide antisera. Table 2 presents data demonstrating that antipeptide antisera containing antibodies of this invention are able to cross-neutralize heterologous virus.

TABLE 2

Cross-Neutralization of Other Influenza Viruses By Antipeptide Antiserum

| Serum | Virus[1] Subgroup | | | | | | | |
|---|---|---|---|---|---|---|---|---|
| | A (H3N2) | B (H1N1) | C (H1N1) | D (H3N2) | E (H1N1) | F (H3N2) | G (H3N2) | H |
| X-47 | 1260 | 10–20 | 0 | 1260 | 0 | 1260 | 1260 | 0 |
| 5 | 20–40 | 2.5–5 | 0 | 5–10 | 2.5* | 2.5–5 | 20–40 | 0 |
| 20 | 10–20 | 5–10 | 0 | 10–20 | 2.5–5 | 2.5–5 | 20–40 | 0 |
| 23 | 20–40 | 10–20 | 5–10 | 10–20 | 10–20 | 20–40 | 40–80 | 10–20 |
| 24 | 40–80 | 20–40 | 2.5–5 | 10–20 | 20–40 | 20–40 | 40–80 | 10–20 |
| 26 | 40–80 | 20–40 | 2.5–5 | 20–40 | 10–20 | 10–20 | 40–80 | 10–20 |
| NRS[2] | 0 | 0 | 0 | 0 | 0 | 0 | 0 | 0 |

[1]Virus: A = X-47; B = A/WSN/33; C = A/Swine/76/1; D = A/ENG/42/2; E = A/USSR/90/77; F = A/PC/1/73; G = A/Aichi/2/68; and H = B/HK/8/73.
[2]Normal rabbit serum.
*Less than the numerical value shown.

Other H3 strains show patterns of neutralization similar to those of X-47. In contrast, the H1 strains were not neutralized by the very high titered anti-X-47 virus serum, but they were neutralized by at least some of the antipeptide sera. Antipeptide sera to synthetic peptides 23, 24 and 26 were particularly effective. The degree to which A/WSN/33 (Virus B; H1N1) was neutralized by anti-X-47 antiserum was insignificant compared to the performance of the antivirus antiserum towards H3 subtype viruses. For those viruses for which HA sequences are available, the results appear to be in accord with the degree of amino acid sequence homology between the H1 and H3 subtypes.

We have demonstrated that synthetic peptides corresponding to specific regions of the influenza virus hemagglutinin elicit a neutralizing antibody response to the homologous virus. In addition, combinations of neutralizing antibodies sum together to produce a stronger neutralizing serum. Thus, simultaneous immunization with two or more peptides results in a serum capable of concerted neutralization at multiple sites. Groups of inactive sera do not synergistically combine to neutralize virus, indicating that merely binding a number of large antibody molecules to exposed portions of the HA is not sufficient to block infection and replication.

The data imply that it is necessary to bind antibody to a site functional in the infection and replication process or to a structurally distinct site such as that formed by a disulfide bridge. The relatively low titers of the antipeptide sera relative to the anti-X-47 virus antiserum was probably a function of the limited proportion of antibodies in the antipeptide antiserum recognizing the conformation that the corresponding amino acid sequence attains in the infectious virus. In addition, the anti-X-47 virus antiserum contains antibodies to other viral components, e.g., neuramidase, which may enhance the neutralizing activity of the HA antibodies in this serum.

In our studies, we have shown a good degree of cross-reactivity (cross-neutralization) of some of our antisera against synthetic HA peptides corresponding to regions of the influenza HA molecule (H3 subtype) towards variants of the H3 subtype as well as representatives of other influenza A virus HA subtypes and one influenza B virus. This is particularly intriguing as the anti-X-47 virus antiserum, which has a much higher neutralizing titer than the antipeptide sera towards X-47 virus, shows no activity or greatly reduced activity toward heterologous viruses. In addition, previous work by Green et al., above, showed that anti-X-47 virus antiserum did not recognize any of the synthetic peptides. The reason for this discrepancy may be due to the limited immunogenicity of the intact virus, or the effect of carbohydrate on the immune response to the intact virus.

These data imply that the immune response towards intact virus (as in conventional immunization) is considerably different than can that obtained with synthetic peptides, and that the latter, if one choses peptide immunogens judiciously, can be used effectively for generalized vaccination against influenza.

The amino acid residue sequences of the above, cross-reacting, peptides are illustrated in the formulas below, from left to right and in the direction from amino-terminus to carboxy terminus:

Peptide 5 CNNPHRIL;
Peptide 20 CPKYVKQNTLKLATGMRNVPEKQTR;
Peptide 23 SIMRSDAPIGTCSSECITPNGSIPNDKPFQNVNKITY;
Peptide 24 RGIFGAIAGFIENGWEGMIDGWYGFRHQN;
Peptide 26 EKQTRGIFGA.

As can be seen from examination of FIG. 1, peptide 5 corresponds in amino acid residue sequence to positions 53–60 from the amino-terminus of the $HA_1$ molecule of the X-47 influenza virus; peptide 20 corresponds in amino acid residue sequence to positions 306–330, from the amino-terminus and includes the carboxy-terminus of the $HA_1$ molecule of X-47; peptide 23 corresponds in amino acid residue sequence to positions 267–300 from the amino-terminus of the $HA_1$ molecule of X-47; peptide 24 corresponds in amino acid residue sequence to position 330, the carboxy-terminus, of the $HA_1$ molecule through position 29 from the amino-terminus of the $HA_2$ molecule of X-47; and peptide 26 corresponds to position 326 from the amino-terminus of the $HA_1$ molecule through the carboxy-terminus (position 330) and to position 6 of the $HA_2$ molecule of X-47.

It is believed that synthetic peptides whose amino acid residue sequences correspond to the above amino acid residue positions in hemagglutinin molecules of strains of influenza virus other than X-47 and listed in Table 2 also induce production of antibodies that cross-react and neutralize at least some of the influenza strains or subtypes of Table 2, above, in addition to neutralizing the strain or subtype to a portion of whose hemagglutinin molecule amino acid residue sequence such peptides correspond.

While not wishing to be bound by theory, it is thus believed that production of cross-reactive, neutralizing antibodies induced by immunization with synthetic peptides is a function of the positional sequence of the immunizing synthetic peptide. Consequently, cross-reactive, neutralizing antibodies can be induced by immunization with a synthetic peptide whose amino acid residue sequence corresponds to the homologous amino acid residue sequences of the positions on the hemagglutinin molecule of peptides 5, 20, 23, 24 or 26.

It is also noted that the positions of the above peptides are approximate and may be varied in either direction by up to about three amino acid residues so long as the peptide contains about 8 to about 40 amino acid residues and the sequence of those peptide residues corresponds to the sequence of one of the above peptides. The word "corresponds" when used in conjunction with amino acid residue sequences means that the sequences of two peptides or of a peptide and protein are so similar that antibodies raised to a peptide of this invention cross-react and bind to both that peptide and to a second corresponding peptide or to a corresponding protein. Preferably the amino acid residue sequences are identical, although strict identity of sequences is not required. For example, conservative changes between amino acid residues such as lysine and arginine, or glutamic acid and aspartic acid, or leucine and isoleucine may be made. In addition, additions and deletions of residues in the sequences may be made without destroying the cross-reactive antibody binding.

C. Human T-Cell Responses

Protection of an animal host typically involves both the participation of antibody-producing B-cells (humoral response) and of T-cells that have a variety of functions (cellular responses). The above-described results relate primarily to B-cell stimulation of antibody production.

Further work has been conducted to assess the effect on T-cell proliferation of the peptides of this invention. That work is reported in Lamb et al., *Nature*, 300, 66–69 (1982), the disclosures of which are incorporated herein by reference.

Briefly, the results shown in Lamb et al. indicate that synthetic peptide 20 was particularly effective in inducing proliferation of T-cell clones derived from peripheral blood lymphocytes from human donors selected for known responses to strain A influenza virus (A/Texas/1/77; H3N2). The sequence of peptide 20 is distant from the proposed antibody binding sites, but appears to be immunodominant for cellular responses to the virus.

The amino acid residue sequence of peptide 20 is shown in FIG. 1 and above in Section B.

Peptide 20 corresponds in amino acid residue sequence to positions 306 through 330, the carboxy-terminus of the $HA_1$ molecule. Stated differently, this peptide extends from the carboxy-terminus of the $HA_1$ toward the amino-terminus of the $HA_1$ to the residue adjacent the carboxy-terminal-most cysteine (cysteine 306) in the $HA_1$. In the intact $HA_1$ molecule, cysteine 306 exists as a portion of a cystine residue forming a disulfide bond with the residue at position 282. Thus, cysteine 306 is more accurately referred to as half-cystine 306, as is known in the art. It is believed that this region of the $HA_1$ molecule is a region (position 306–330, or the position of the carboxy-terminus to the first half-cystine on the $HA_1$ molecule) that stimulates T-cell proliferation in influenza viruses generally.

Another embodiment of this invention utilizes a peptide whose amino acid sequence corresponds to the amino acid residue sequence of synthetic peptide 20 alone or as a conjugate to stimulate T-cell proliferation and/or to also induce antibody production by B-cells. That peptide can be used for those purposes or it can be used in conjunction with one or more additional peptides or their conjugates to stimulate both T-cells and B-cells to provide both cellular as well as humoral responses.

D. Protection of Host Animals $CAF_1$ mice were immunized with a mixture of six synthetic peptide conjugates whose sequences corresponded to amino acid residue sequences throughout the $HA_1$ molecule. Each mouse was given three injections containing 20 micrograms of mixed peptide each in complete Fruend's adjuvant. Serum titers after five weeks ranged from zero through 320 using the ELISA assay discussed by Green et al., above. Analogous rabbit titers would have been about 5120.

Despite the seemingly low titers observed, protection upon intranasal challenge with infectious influenza virus was observed. Thus, in the control group that received injections of saline and complete Freund's adjuvant, 9 of 15 animals (60%) died, while only 3 of 15 animals (20%) died in the peptide-immunized (vaccinated) groups.

The peptide mixture utilized in the above protection determination contained peptides 2, 4, 7, 11, 19 and 20 (Table 1) in approximately equal amounts. Each peptide was conjugated to KLH.

The vaccination protocol for the above determinations was as follows. Groups of 4-week old $CAF_1$ male mice were vaccinated with the peptide-containing vaccine or saline-containing vaccine in complete Freund's adjuvant on days 0, 14 and 28. Animals were bled to obtain serum titer data on day 35, and then challenged on day 38 with an intranasal inoculation of mouse-adapted X-47 influenza virus at a concentration designed to deliver an $LD_{50}$–$LD_{80}$; i.e., to kill 50% to 80% of the population.

The challenged animals were then housed in an isolation facility and examined daily for signs of disease. After three weeks of isolation, the perecent mortality was calculated and compared to the control group.

Depending on their length, the peptides were used alone or as a conjugates with KLH. Depending on their solubilites, peptides containing fewer than about 34 residues were typically used as conjugates while peptides longer than 35 residues were typically used alone.

E. Carrier Systems

As noted previously, and shown in Table 1, the peptides of this invention may be used alone or linked (coupled) to a carrier as a conjugate. Keyhole limpet hemocyanin (KLH) was used as the carrier of the conjugates used to obtain the results of Table 1. Additional carriers useful in preparing conjugates includes, but are not limited to, agarose, cross-linked agarose, edestin, curcubin, bovine serum albumin, human serum albumin, red blood cells such as sheep erythrocytes, and polyamino acids such as poly (D-lysine: D-glutamic acid).

Immunizations utilizing conjugates have been found to be more effective than similar immunizations using the peptide alone, and not coupled to a carrier. A study was therefore carried out to examine the effects of the carrier on the B-cell, neutralizing antibody-producing (humoral) response in mice.

The peptide used in these studies was synthetic peptide 20 which contains a Cys residue at its amino-terminus. The carriers in these studies were thiopropyl-Sepharose 6B and thiopropyl-Sepharose 4B available from Pharmacia Fine Chemicals, Piscataway, N.J.

The data from these studies shown in Table 3, below, illustrate that both carriers were immunogenically effective. In fact, the Sepharose 6B conjugates were about as effective as was the X-47 virus itself since the titers obtained by ELISA assay (Green et al., above) of antisera raised in response to those conjugates was of the same order of magnitude as the titers obtained using the virus (about 1600–3200).

TABLE 3

Anti-X-47 ELISA Titers of Mice Immunized With Sepharose-Coupled Peptide 20

| Mouse Number | X-47 Titer |
|---|---|
| Group 1: 3 ip/sq injections[1] of Sepharose 6B-Peptide 20 (at 50 micrograms of peptide (conjugate)/mouse with 4 milligrams of alum) | |
| 1 | 1280 |
| 2 | 160 |
| 3 | 320 |
| 4 | 1280 |
| 5 | 2560 |
| Group 2: 3 sq injections[2] of Sepharose 6B-Peptide 20 (at 50 micrograms of peptide (conjugate)/mouse with CFA[3] at 5 milligrams mycob[4]) | |
| 6 | 640 |
| 7 | 640 |
| 8 | 80 |
| 9 | 1280 |
| 10 | 20* |
| Group 3: 1 ip/sq injection[1] of Sepharose 4B-Peptide 20 (at 50 micrograms of peptide (conjugate)/mouse with 4 milligrams of alum) | |
| 11 | 0 |
| 12 | 0 |
| 13 | 80 |
| 14 | 0 |
| Group 4: 3 sq injections[2] of Sepharose 4B-Peptide 20 (at 50 micrograms of peptide (conjugate)/mouse with CFA[3] at 5 milligrams mycob[4]) | |
| 15 | 20* |
| 16 | 20* |
| 17 | 1280 |

TABLE 3-continued

Anti-X-47 ELISA Titers of Mice Immunized With Sepharose-Coupled Peptide 20

| Mouse Number | X-47 Titer |
|---|---|
| 18 | 1280 |
| 19 | 20* |

[1]ip/sq = One intraperitioneal injection, and four subcutaneous injections (one subcutaneous injection in each hip and in each shoulder).
[2]sq = Four subcutaneous injections as described above.
[3]CFA = complete Freund's adjuvant.
[4]Mycob = Mycobacterium Tuberculosis H37RA added to the adjuvant.
*Less than the numerical value shown.

The Sepharose carriers have several advantages over KLH as a carrier. These materials have a solid phase composed of cross-linked polysaccharide chains (agarose), a spacer moiety and a protected thiol group (prior to the linking reaction with the peptide). The 2-thiopyridyl protecting moiety is easily substituted by the cysteine -SH groups available in synthetic peptides. The substitution reaction occurs in saline solution, requires no coupling agent, is efficient (Sepharose 6B: yields=-60-65%; Sepharose 4B yield=40%), and it is easily monitored by an increase in absorption at 343 nanometers due to the liberation of 2-thiopyridone.

Thiopropyl Sepharose 6B has a higher binding capacity, a greater binding efficiency, e.g. yield of 60–65% vs. 40%, and shows apparently more immunogenicity as compared to thiopropyl Sepharose 4B. In addition, as a potential human vaccine, the immunogenicity of the thiopropyl Sepharose 6B - peptide 20 conjugate was greater in the presence of alum which can be used in humans than in the presence of compute Freund's adjuvant (CFA) which is not used for human vaccines.

Peptides were coupled to Sepharose carriers in deaerated 0.01 molar phosphate buffer solution additionally containing 0.5 molar NaCl, 0.001 molar ethylene diaminethetracetic acid and 0.2 percent $NaN_3$ at a pH value of 7. For couplings to Sepharose 4B, 1 milliliter of packed, swollen Sepharose 4B was added to 2 milliliters of the phosphate buffer further containing 5 milligrams per milliliter of peptide. For couplings to Sepharose 6B, 0.5 milliliters of packed, swollen Sepharose 6B was added to 5 milliliters of the phosphate buffer further containing 5 milligrams per milliliter of peptide. The reaction solutions were gently agitated at a temperature of 4° C. overnight, and the coupled products were preferably washed with the buffer prior to use.

While the Sepharose-based and alum systems provide several advantages with regard to human vaccination, the use of KLH as carrier and CFA as a diluent/adjuvant in immunizations provides a useful system for comparisons of data on other variables. Such a system was used to assess the effect of a single immunization protocol using synthetic peptide 20 as the immunogen: The results are shown in Table 4, below.

TABLE 4

Immune Response to a Single Injection of KLH-Peptide 20 in CFA[1]

| Mouse Number | Peptide Amount[2] | Anti-X-47 Titers[3] at Weeks | | | | | |
|---|---|---|---|---|---|---|---|
| | | 1 | 2 | 3 | 4 | 6 | 7 |
| 1 | 5 | — | — | — | — | — | — |
| 2 | 5 | 0 | 0 | 0 | 0 | 0 | 0 |
| 3 | 5 | 0 | 0 | 0 | 0 | 640 | 1600 |
| 4 | 5 | 0 | 20* | 0 | 0 | 0 | 0 |
| 5 | 5 | 20* | 20* | 0 | 0 | 80 | 800 |
| 6 | 20 | 0 | 20* | 20* | 20* | 3200 | 6400 |
| 7 | 20 | 20* | 20* | 20* | 20* | 1280 | 1600 |
| 8 | 20 | 0 | 20* | 20 | 20* | 6400 | 6400# |
| 9 | 20 | 0 | 20* | 1280 | 1280 | 3200 | 6400 |
| 10 | 20 | 20* | 40 | 2560# | 1280 | 6400 | 6400 |
| 11 | 40 | 20* | 20* | 1280 | 1280 | 6400# | 6400# |
| 12 | 40 | 0 | 20* | 80 | 160 | 3200 | 6400 |
| 13 | 40 | 0 | 0 | 20 | 160 | 6400 | 6400 |
| 14 | 40 | 20* | 0 | 640 | 1280 | 3200 | 6400 |
| 15 | 40 | 0 | 20* | 2560# | 2560# | 6400# | 6400# |

[1]Conjugates were prepared from about 40–50 micrograms of peptide and about 25–32 micrograms of KLH as described in Green et al., Cell, 28, 477–487 (1982). 100 Percent reaction was presumed. The immunization was carried out in complete Freunds' adjuvant that contained 0.6 milligrams of Mycobacterium Tuberculosis per mouse in a total volume of 0.2 milliliters per mouse.
[2]The amount of peptide in micrograms in each KLH conjugate that was injected.
[3]Titers performed in ELISA assays as described in Green et al., Cell, 28, 477–487 (1982) at the weeks indicated after immunizations were carried out.
*Titer less than the numerical value shown.
Titer greater than the numerical amount shown.

The above data illustrate that significant amounts of antibodies reactive with X-47 influenza virus were induced in the mice three weeks after they were immunized with the KLH-peptide 20 conjugate. Those titers continued to increase over the next four weeks, as shown, and peaked in the period of 8–12 weeks after immunization. Six months after the single injection, titers from mice that received the 5 micrograms doses were about 800 to about 3200; titers in the mice that received the 20 microgram doses were about 800 to more than about 6400; and titers in mice that received the 40 microgram doses were about 3200 to more than 6400. Our previously discussed work with intranasal challenges using the X-47 virus indicated that mice having antibody titers in the above, six-month, ranges were protected against infection by the virus.

The above data from a single immunization appear to be superior to the results obtained using a multidose protocol. The pattern of peak titers appearing at 8–12 weeks followed by a slow decline suggests that a single injection of peptide immunogen may be sufficient to induce long term immunity to influenza.

F. Cyclized Peptides

Cyclic peptides whose amino acid residue sequences correspond to $HA_1$ positions 306 to 330 (carboxy-terminus; peptide 20) and to $HA_1$ positions 140 to 160 [antigenic Site A identified by Wiley et al., Nature, 289, 373–378 (1981)] were also prepared. The first synthesized, straight chain cyclic peptide-precursors contained cysteine residues at the amino- and carboxy-terminii which were subsequently oxidized to form cyclic and/or oligomeric materials that are also referred to herein as cyclic peptides in as much as oxidations were continued until no free mercaptan could be detected by the Ellman test [Ellman, Arch. Biochem. Biophys., 82, 7077 (1959)], thereby indicating that there were substantially no free —SH groups at peptide terminii.

The conformation of peptide 20 in the native hemagglutinin molecule is relatively linear. The region of positions 140–160 of the hemagglutinin forms a natural loop conformation in the native protein.

Analysis of variants has shown the position 140–160 loop to be important in the generation of antibodies against the native hemagglutinin. However, linear peptides corresponding to that region, e.g. peptide 15 (corresponding to positions 140-156), have consistantly failed to induce the production of antibodies that react with the intact virus, although those antibodies do react with the hemagglutinin.

The cyclic peptides were prepared by dissolving the peptides in a 0.1 molar bicarbonate solution. Cyclic, monomeric or substantially monomeric peptides were prepared by dissolution of the peptide at a concentration of 0.1 milligrams per milliliter, while the oligomeric material was prepared at a concentration of 10 milligrams per milliliter. The peptide solutions so prepared were stirred overnight while being exposed to atmospheric oxygen to effect the cyclizing oxidations. The oxidized solutions were thereafter tested for completeness of reaction and then lyophilized. The dried materials so prepared were thereafter used for immunizations.

Using the above discussed ELISA, rabbit and mouse antibodies to linear peptide 20 were shown to recognize cyclized peptide 20, and particularly the oligomeric form of peptide 20. Antibodies to the X-47 virus did not bind to the cyclized peptide. Similarly, the anti-X-47 sera did not bind to the cyclized peptide corresponding to the Site A loop structure.

In summary, in its more specific embodiment, this invention comprises specifically defined peptides. It will be understood by those in the art that minor deviations from the exact sequences of the above-disclosed peptides may be made without substantially impairing the immunological characteristics of the peptides.

The neutralizing and protective antibody-producing peptides of this invention contain the following amino residue acid sequences, from left to right and in the direction of amino-terminus to carboxy terminus, (a) SIMRSDAPIGTCSSECITPNGSIPNDKPFQNVNKITY;
(b) RGIFGAIAGFIENGWEGMIDGWYGFRHQN;
(c) EKQTRGIFGA;
(d) CPKYVKQNTLKLATGMRNVPEKQTR;
(e) CNNPHRIL;
(f) CPKYVKQNTLKLATGMRNVPEKQTRC; and
(g) CKRGPDSGFFSRLNWLYKSGSC in oxidized, cyclic or oligomeric form.

II. Receptor Molecules

Biologically active receptor molecules constitute another embodiment of this invention. These molecules are antibodies, or idiotype-containing polyamide portions of antibodies, induced or raised to a synthetic peptide of this invention or to its conjugate with a carrier. In preferred practice, the receptors are raised to the preferred synthetic peptides of this invention.

The receptors are biologically active in that they bind at least with the synthetic peptide when admixed therewith in aqueous solution, at least at physiological pH values and ionic strengths. Preferably, the receptors also bind with the naturally occurring virus or the hemaglutinin molecule under the same conditions. It is more preferred that the receptors bind to the synthetic peptide, hemagglutinin and virus within a pH value range of about 5 to about 9, and at ionic strengths such as that of distilled water to that of about one molar sodium chloride.

Idiotype-containing polyamide portions of antibodies are the portions of antibodies that bind to an antigen. Such portions include the Fab, Fab', and F(ab')$_2$ fragments prepared from antibodies by well-known enzymatic cleavage techniques. Inasmuch as antibodies are discussed in the art as being "raised" or "induced", idiotype-containing polyamide portions of antibodies will also be discussed herein as being "raised" or "induced" with the understanding that a subsequent cleavage step is normally required to prepare such materials from antibodies.

The receptor molecules may be polyclonal as is the case for the antibodies in antisera discussed hereinbefore, or the receptors may be monoclonal. Techniques for preparing monoclonal antibodies are well known, and monoclonal receptors of this invention may be prepared by using the synthetic peptides of this invention, preferably coupled to a carrier, as the immunogen as was done by Arnheiter et al., Nature, 294, 278-280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" the synthetic peptides of this invention or their conjugates with a carrier.

Receptors are utilized along with an "indicating group", also sometimes referred to as a "label". The indicating group or label is utilized in conjunction with the receptor as a means for determining whether an immune reaction has taken place, and in some instances for determining the extent of such a reaction.

The indicating group may be a single atom as in the case of radioactive elements such as iodine 125 or 131, hydrogen 3 or sulfur 35, or elements active in nuclear magnetic resonance (NMR) spectroscopy such as fluorine 19 or nitrogen 15. The indicating group may also be a molecule such as a fluorescent dye like fluoresein, or an enzyme, such as horseradish peroxidase (HRP), or the like.

The indicating group may be bonded to the receptor as where an antibody is labeled with 125$_I$. The indicating group may also constitute all or a portion of a separate molecule or atom that reacts with the receptor molecule such as HRP-linked to goat anti-rabbit antibodies where the antibody receptor was raised in a rabbit, or where a radioactive element such as 125$_I$ is bonded to protein A obtained from *Staphylococcus Aureus*.

Where the principal indicating group is an enzyme such as HRP, additional reagents are required to visualize the fact that an immune reaction has occurred. Such additional reagents for HRP include hydrogen peroxide and an oxidation dye precursor such as diaminobenzidine or 2,2'-azino-di-(3ethybenzthiazoline sulfate) from whom? + Where city, state or country, used herein.

The terms "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

Industrial Application

Safe and effective synthetic peptide vaccines can be produced against influenza and the design of a more universal vaccine is a realistic possibility. Vaccination with these peptide immunogens may lead to their own patterns of genetic drift. However, if the peptides are chosen with regard to a site functionally necessary for viral replication, resulting mutations in those regions may well be lethal.

What is claimed is:

1. A peptide having an amino acid residue sequence that corresponds to the sequence, form left to right and in the direction of amino-terminus to carboxy-terminus, of the formula

SIMRSDAPIGTCSSECITPNGSIPNDKPFQNVNKITY.

2. A peptide having an amino acid residue sequence that corresponds to the sequence, for left to right and in the direction of amino-terminus to carboxy-terminus, of the formula

RGIFGAIAGFIENGWEGMIDGWYGFRHQN.

3. A peptide having an amino acid residue sequence that corresponds to the sequence, from left to right and in the direction of amino-terminus to carboxy-terminus, of the formula

EKQTRGIFGA.

4. A peptide conjugate containing a peptide coupled to a carrier that is capable of inducing the production of antibodies that (a) neutralize the influenza virus subtype to a portion of whose hemagglutinin molecule amino acid residue sequence said peptide corresponds as well as (b) cross-neutralize a second influenza virus of a second subtype, the peptide of said conjugate having an amino acid residue sequence that corresponds to the sequence, from left to right and in the direction of amino-terminus to carboxy-terminus, of the formula

SIMRSDAPIGTCSSECITPNGSIPNDKPFQNVNKITY.

5. A peptide conjugate containing a peptide coupled to a carrier that is capable of inducing the production of antibodies that (a) neutralize the influenza virus subtype to a portion of whose hemagglutinin molecule amino acid residue sequence said peptide corresponds as well as (b) cross-neutralize a second influenza virus of a second subtype, the peptide of said conjugate having an amino acid residue sequence that corresponds to the sequence, from left to right and in the direction of amino-terminus to carboxy-terminus, of the formula

RGIFGAIAGFIENGWEGMIDGWYGFRHQN.

6. A peptide conjugate containing a peptide coupled to a carrier that is capable of inducing the production of antibodies that (a) neutralize the influenza virus subtype to a portion of whose hemagglutinin molecule amino acid residue sequence said peptide corresponds as well as (b) cross-neutralize a second influenza virus of a second subtype, the peptide of said conjugate having an amino acid residue sequence that corresponds to the sequence, from left to right and in the direction of amino-terminus to carboxy-terminus, of the formula

EKQTRGIFGA.

7. A receptor molecule raised to a peptide having an amino acid residue sequence that corresponds to the sequence, from left to right and in the direction of amino-terminus to carboxy-terminus, of the formula

SIMRSDAPIGTCSSECITPNGSIPNDKPFQNVNKITY.

8. A receptor molecule raised to a peptide having an amino acid residue sequence that corresponds to the sequence, for left to right and in the direction of amino-terminus to carboxy-terminus, of the formula

RGIFGAIAGFIENGWEGMIDGWYGFRHQN.

9. A receptor molecule raised to a peptide having an amino acid residue sequence that corresponds to the sequence, from left to right and in the direction of amino-terminus to carboxy-terminus, of the formula

EKQTRGIFGA.

* * * * *